(12) United States Patent
Guth et al.

(10) Patent No.: US 9,789,063 B2
(45) Date of Patent: *Oct. 17, 2017

(54) STORAGE-STABLE DUST-FREE HOMOGENEOUS PARTICULATE FORMULATION

(71) Applicant: BASF SE, Ludwigshafen (DE)

(72) Inventors: Felicitas Guth, Neustadt (DE); Karl Kolter, Limburgerhof (DE); Michael Schönherr, Frankenthal (DE); Michael Klemens Müller, Haßloch (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/036,365

(22) Filed: Sep. 25, 2013

(65) Prior Publication Data

US 2014/0086992 A1 Mar. 27, 2014

Related U.S. Application Data

(60) Provisional application No. 61/706,133, filed on Sep. 27, 2012.

(51) Int. Cl.
| | |
|---|---|
| A61K 9/00 | (2006.01) |
| A61K 47/00 | (2006.01) |
| A61K 9/16 | (2006.01) |
| A61K 47/22 | (2006.01) |
| A61K 47/32 | (2006.01) |

(52) U.S. Cl.
CPC .......... *A61K 9/1617* (2013.01); *A61K 9/1682* (2013.01); *A61K 47/22* (2013.01); *A61K 47/32* (2013.01)

(58) Field of Classification Search
CPC ...... A61K 47/22; A61K 47/32; A61K 9/1617; A61K 9/1682
See application file for complete search history.

(56) References Cited

U.S. PATENT DOCUMENTS

| | | | |
|---|---|---|---|
| 3,102,078 A | 8/1963 | Robeson | |
| 4,395,422 A * | 7/1983 | Schmidt | A61K 47/42 514/458 |
| 4,603,143 A | 7/1986 | Schmidt | |
| 5,179,122 A | 1/1993 | Greene et al. | |
| 5,891,469 A | 4/1999 | Amselem | |
| 5,891,845 A * | 4/1999 | Myers | 424/451 |
| 6,569,463 B2 * | 5/2003 | Patel | A61K 9/1617 424/422 |
| 6,599,528 B1 | 7/2003 | Rosenberg et al. | |
| 6,923,988 B2 * | 8/2005 | Patel | A61K 9/1617 424/422 |
| 2003/0206978 A1 * | 11/2003 | Sherwood | A61K 9/1611 424/728 |
| 2003/0236236 A1 | 12/2003 | Chen et al. | |
| 2005/0208082 A1 | 9/2005 | Papas et al. | |
| 2005/0236236 A1 | 10/2005 | Farooq | |
| 2006/0057073 A1 * | 3/2006 | Lintz et al. | 424/45 |
| 2006/0198814 A1 * | 9/2006 | Gruening et al. | 424/78.3 |
| 2007/0128289 A1 * | 6/2007 | Zhao | 424/489 |
| 2010/0011610 A1 * | 1/2010 | Bittorf | F26B 3/08 34/359 |
| 2012/0225953 A1 | 9/2012 | Berndl et al. | |
| 2013/0236505 A1 * | 9/2013 | Kolter | A61K 47/32 424/400 |

FOREIGN PATENT DOCUMENTS

| | | | |
|---|---|---|---|
| EP | 1880715 | 1/2008 | |
| WO | WO-00/57854 | 10/2000 | |
| WO | WO-01/00175 | 1/2001 | |
| WO | WO-01/91727 | 12/2001 | |
| WO | WO-2005/039551 | 6/2005 | |
| WO | WO 2006036614 A2 * | 4/2006 | ............. A61K 9/146 |
| WO | WO-2007/019058 | 2/2007 | |
| WO | WO-2008/009689 | 1/2008 | |
| WO | WO-2009/130204 | 10/2009 | |

OTHER PUBLICATIONS

Gianfrancesco. Powder agglomeration during the spray-drying process: measurements of air properties. Dairy Sci. Technol. 88 (2008) 53-64.*
Turchiuli. Evolution of particle properties during spray drying in relation with stickiness and agglomeration control. Powder Technology 208 (2011) 433-440.*
Pietsch. Chapter 6. Industrial Applications of Size Enlargement by Agglomeration. In: Agglomeration in Industry. 2005. p. 218.*
PCT International Search Report in PCT/EP2013/069111, dated Nov. 5, 2013, 4 pgs.
Non-Final Office Action in U.S. Appl. No. 14/036,445, dated Feb. 26, 2014, 12 pages.

* cited by examiner

*Primary Examiner* — Robert A Wax
*Assistant Examiner* — Olga V Tcherkasskaya
(74) *Attorney, Agent, or Firm* — Marshall, Gerstein & Borun LLP

(57) ABSTRACT

Described is a storage-stable dust-free homogeneous particulate formulation. The formulation consists of (a) at least one water-soluble Vitamin E-derivative, (b) at least one hydrophilic polymer, (c) optionally additional surface-active substances, and (d) optionally additional pharmaceutical additives. The sum of (a), (b), (c) and (d) equals 100% by weight of the formulation. The fines fraction with particle diameters of less than 100 μm is less than 10% by weight. Describe also is a process for manufacturing the formulation, and use of the formulation as a solubilizing composition in pharmaceutical formulations.

21 Claims, No Drawings

STORAGE-STABLE DUST-FREE HOMOGENEOUS PARTICULATE FORMULATION

CROSS-REFERENCE TO RELATED APPLICATIONS

This application claims the benefit of priority under 35 U.S.C. §119(e) to U.S. Provisional Application No. 61/706,133, filed Sep. 27, 2012, the entire content of which is incorporated herein by reference in its entirety.

TECHNICAL FIELD

The present invention relates to a storage-stable dust-free homogeneous particulate formulation. The invention also relates to a process for manufacturing the formulation, and the use of the formulation as a solubilizing composition in pharmaceutical formulations. Specifically, the invention relates to a storage-stable dust-free homogeneous particulate formulation, comprising at least one water-soluble Vitamin E-derivative, at least one hydrophilic polymer, optionally additional surface-active substances, and optionally additional pharmaceutical additives, with a fraction of fines passing through a sieve with a mesh size of 100 μm of less than 10%-b.w.

BACKGROUND

It is known that surfactants can be used for enhancing the solubility of hydrophobic active ingredients in an aqueous medium and thus improve bioavailability of the active ingredient.

Among the various surfactants water-soluble vitamin E derivatives are known as potential agents for enhancing solubility. Well known water-soluble Vitamin E-derivatives are tocopheryl polyethylene glycol succinates, for instance a tocopheryl polyethylene 1000 succinate (TPGS). It is known for example from U.S. Pat. No. 3,102,078 that TPGS can be used as a solubilizing agent for fat-soluble vitamins.

Due to their waxy nature tocopheryl polyethylene glycol succinates are difficult to handle. Many attempts have been made to overcome this disadvantage.

U.S. Pat. No. 5,179,122 describes a solid composition where TPGS is absorbed or adsorbed to an inert carrier such as microcrystalline cellulose, starch or inorganic materials.

WO 01/00175 discloses mechanically stable pharmaceutical dosage forms which are solid solutions of active ingredients in an auxiliary agent matrix. The matrix contains a homopolymer or a copolymer of N-vinylpyrrolidone and a liquid or semi-solid surfactant.

WO 01/91727 discloses a self-emulsifying active substance formulation comprising at least one active substance and a formulation basis which includes a lipid component, a binder component and optionally additional auxiliary agents.

WO 00/57854 discloses mechanically stable pharmaceutical dosage forms comprising plastically mouldable, matrix-forming auxiliaries and more than 10 and up to 40% by weight of a surface-active substance with an HLB of between 2 and 18 that is liquid at 20° C., or has a drop point at between 20 and 50° C. The auxiliaries are prepared by spray-drying or melt extrusion.

WO 2005/039551 discloses a solid pharmaceutical dosage form providing improved oral bioavailability for inhibitors of HIV protease. The dosage form comprises a solid dispersion of at least one HIV protease inhibitor and at least one pharmaceutically acceptable water-soluble polymer and at least one pharmaceutically acceptable surfactant, said pharmaceutically acceptable water-soluble polymer having a Tg of at least about 50° C.

U.S. 2005/0208082 discloses a solubilizing composition comprising a mixture of vitamin E TPGS and linoleic acid.

U.S. 2003/0236236 discloses pharmaceutical compositions for administration of hydrophobic drugs comprising a hydrophobic drug, a vitamin E substance and a surfactant.

WO 2008/009689 discloses a solubilizing composition comprising a polyalkylene glycol derivative of a tocopheryl compound and at least one polyalkylene glycol fatty acid monoester or diester. The composition is obtained by melt-extrusion of the components.

WO 2009/130204 discloses solid compositions comprising permeability improving substances embedded in a water-soluble matrix. The compositions are obtained by normal spray-drying processes.

Known products still do not satisfy the requirements needed for safe and reliable manufacture of pharmaceutical formulations or dosage forms. Because of the tackiness of and relatively high amount of fines, the material is not free-flowing and tends to block dosage systems and other parts of the machinery. Another disadvantage of known materials is the tendency to caking and, therefore, reduced storage stability. Yet another problem is phase separation of the waxy surfactant and the hydrophilic polymer, either during manufacture of the solubilizing composition or on storage.

Thus, there is a need for a solubilizing composition based on water-soluble vitamin E-derivatives and hydrophilic polymers that is storage stable, dust-free, free of tackiness, free-flowing, easily miscible and offers good processability in the manufacture of pharmaceutical formulations. In addition, there is a need to avoid organic solvents in manufacture of the solubilizing composition, not only because organic solvents are a safety risk, but also to avoid problems with the allowable residual solvents content.

SUMMARY

A first embodiment is directed to a storage-stable dust-free homogeneous particulate formulation, comprising of (a) at least one water-soluble Vitamin E-derivative, (b) at least one hydrophilic polymer, (c) optionally additional surface-active substances, and (d) optionally additional pharmaceutical additives, with the proviso, that the sum of (a), (b), (c), and (d) equals 100% by weight of the formulation, and wherein the fines fraction with particle diameters of less than 100 μm is less than 10% by weight.

In a second embodiment, the formulation of the first embodiment is modified, wherein the average particle size $D_{0[4,3]}$ is from 100 to 800 μm.

In a third embodiment, the formulation of the first and second embodiments is modified, wherein component (a) comprises a tocopheryl polyethylenglycol succinate.

In a fourth embodiment, the formulation of the first through third embodiments is modified, wherein component (b) is selected from the group consisting of homo- or copolymers of a N-vinyl lactame, cellulose derivatives, poly acrylic polymers, polyalkylene oxids, polyvinyl alcohols, and oligo- and polysaccharides.

In a fifth embodiment, the formulation of the first through fourth embodiments is modified, wherein component (b) comprises a homo- or copolymer of a N-vinyl lactame.

In a sixth embodiment, the formulation of the first through fifth embodiments is modified, wherein component (b) comprises a homo- or copolymer of N-vinyl pyrrolidone.

In a seventh embodiment, the formulation of the first through sixth embodiments is modified, wherein component (b) comprises a copolymer of N-vinyl pyrrolidone and vinyl acetate.

In an eighth embodiment, the formulation of the first through seventh embodiments is modified, wherein component (b) comprises a copolymer of N-vinyl caprolactam, vinyl acetate and polyethylene glycol.

In a ninth embodiment, the formulation of the first through eighth embodiments is modified, wherein component (b) comprises a cellulose derivative.

In a tenth embodiment, the formulation of the first through ninth embodiments is modified, wherein component (c) is selected from the group consisting of polyalkylene glycol fatty acid esters, polyalkylene glycol fatty alcohol ethers, polyalkylene glycols, poloxamers, polyalkylene glycol glycerides, and alkylene glycol fatty acid mono- and diesters.

In an eleventh embodiment, the formulation of the first through tenth embodiments is modified, wherein component (d) is selected from the group consisting of antioxidants, chelating agents, colorants, flavours, fillers, stabilizers, preservatives, and biocides.

In a twelfth embodiment, the formulation of the first through eleventh embodiments is modified, wherein component (d) is selected from ascorbic acid, tocopherol, or butyl hydroxyl toluene.

In a thirteenth embodiment, the formulation of the first through twelfth embodiments is modified, wherein the formulation comprises (a) 5 to 20% b.w. of at least one water-soluble Vitamin E-derivative, (b) 80 to 95% b.w. of at least one hydrophilic polymer, (c) 0 to 15% b.w. of additional surface-active substances, and (d) 0 to 15% b.w. of additional pharmaceutical additives.

In a fourteenth embodiment, the formulation of the first through thirteenth embodiments is modified, wherein the formulation consists of (a) 10 to 20% b.w. of at least one water-soluble Vitamin E-derivative, (b) 80 to 90% b.w. of at least one hydrophilic polymer, (c) 0 to 15% b.w. of additional surface-active substances, and (d) 0 to 15% b.w. of additional pharmaceutical additives.

A fifteenth embodiment is directed to a process for manufacturing the particulate formulation of the first through fourteenth embodiments. The process comprises (i) forming an aqueous solution of components (a), (b), and optionally (c) and (d), and (ii) atomizing said solution with the help of one or more spray nozzles, contacting the atomized solution with particulate material consisting of components (a), (b) and optionally (c) and (d).

In a sixteenth embodiment, the process of the fifteenth embodiment is modified, wherein the particulate formulation is obtained by a spray drying agglomeration, characterized by the following steps: (i) forming an aqueous solution of components (a), (b) and optionally (c) and (d), (ii) atomizing said solution with the help of an atomizing device in a spray tower, contacting the atomized solution with fines of a particulate material consisting of components (a), (b) and optionally (c) and (d) and (iii) separation of the fines and recirculation of the fines into the tower.

In a seventeenth embodiment, the process of the fifteenth and sixteenth embodiments is modified, wherein the process further comprises (iv) drying of the particulate formulation in a fluidized bed.

In an eighteenth embodiment, the process of the fifteenth through seventeenth embodiments is modified, wherein the solids content of the spray solution varies from 10 to 50% b.w.

In a nineteenth embodiment, the process of the fifteenth through eighteenth embodiments is modified, wherein step (i) is carried out by blending an aqueous solution of the hydrophilic polymer (b) into an aqueous solution of component (a).

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Provided is a storage-stable dust-free homogeneous particulate composition, comprising of at least one water-soluble Vitamin E-derivative, at least one hydrophilic polymer, optionally additional surface-active substances, and optionally additional pharmaceutical additives, with a fraction of fines of less than 10% b.w. of particulates with a diameter below 100 μm. According to one or more embodiments, the particulate formulation is obtained by a spray drying agglomeration process using aqueous spray solutions.

According to one or more embodiments, the composition is a storage-stable dust-free particulate formulation, consisting of
(a) at least one water-soluble Vitamin E-derivative,
(b) at least one hydrophilic polymer,
(c) optionally additional surface-active substances, and
(d) optionally additional pharmaceutical additives,
with the proviso, that the sum of (a), (b), (c) and (d) equals 100% by weight of the formulation, and wherein the fines fraction of the particulates is less than 10% by weight of particulates with a diameter below 100 μm.

In one or more embodiments, the composition is a storage-stable dust-free particulate formulation, consisting of
(e) at least one water-soluble Vitamin E-derivative,
(f) at least one hydrophilic polymer,
(g) optionally additional surface-active substances, and
(h) optionally additional pharmaceutical additives,
with the proviso, that the sum of (a), (b), (c) and (d) equals 100% by weight of the formulation, and wherein the fines fraction of the particulates is less than 10 vol.-% of particulates with a diameter below 100 μm, and wherein the average particle size of the particulate formulation as represented by the $D_{0[4,3]}$ value ranges from 120 μm to 500 μm, preferably 80 to 350 μm, most preferably 200 to 300 μm. The average particle size is measured by laser diffraction and represents the volume average.

For all embodiments disclosed herein the bulk densities of the particulate formulations lie in the range of from 0.2 to 0.4 g/cm$^3$, preferably 0.25-0.35 g/cm$^3$.

In one or more embodiments, the angle of repose lies in the range of from 35 to 50° C., preferably 35 to 45° C.

According to one or more embodiments, component (a) is a water-soluble vitamin E-derivative, specifically a polyalkylene glycol derivative, more specifically tocopheryl polyethylene glycol succinates. Suitable polyethylene glycol moieties are those with molecular weights of from 300 to 10.000 g/mol, for example PEG 300, PEG 400, PEG 1000, PEG 15000 or PEG 2000. In one or more embodiments, component (a) comprises a tocopheryl polyethylene glycol 1000 succinate, i.e. a product with a PEG 1000 moiety (TPGS 1000).

In one or more embodiments, the water-soluble vitamin E derivative has a solubility of more than 10% (g/g), preferably more than 25% (g/g) at 20° C.

TPGS 1000 has a solubility in water at 20° C. of more than 25% (g/g) at normal pressure in the range of 0.1 MPa.

In one or more embodiments, the amount of component (a) in the particulate formulation can range from 5 to 20% by weight of the composition, specifically 10 to 20% b.w.

In one or more embodiments, component (b) is selected from the group consisting of homo- or copolymers of an N-vinyl lactame, cellulose derivatives and polyacrylic polymers.

According to one specific embodiment, component (b) is a homo- or copolymer of N-vinyl pyrrolidone. Suitable polyvinyl pyrrolidone homopolymers show K values of from 12 to 100, preferably K 12 to 60 (1% b.w. in water). According to an embodiment component (b) is a copolymer of N-vinyl pyrrolidone and vinyl acetate, specifically a copolymer obtained from 6 parts of N-vinyl pyrrolidone and 4 parts of vinyl acetate (copovidone). The K value of such a copolymer lies in the range of from 20 to 40, particularly 25 to 31.

According to another embodiment, component (b) is a copolymer of N-vinyl caprolactam, vinyl acetate and polyethylene glycol with K-values in the range of from 25 to 50, specifically in a weight ratio of 57:30:13 with a PEG 6000 moiety and with a K-value of 31 to 41 (1% b.w. solution in ethanol), commercially available as Soluplus®, BASF SE.

According to another embodiment, component (b) is a polyacrylate. According to this embodiment component (b) is a copolymer of ethyl acrylate and methacrylic acid in a ratio of 1:1, commercially available as Kollicoat MAE 30 DP or 100P, or copolymers of methyl methacrylate and methacrylic acid in ratios of 1:1 and 2:1 commercially available as Eudragit L and S, or terpolymers of ethyl acrylate, methyl methacrylate and trimethylammonioethyl methacrylate in ratios of 1:2:0.2 or 1:2:0.1 commercially available as Eudragit RL and RS.

According to another embodiment, component (b) is a cellulose derivative, for example hydroxypropyl methyl cellulose acetat succinate (HPMCAS), hydroxypropyl methyl cellulose phthalate, celluloseacetate phthalate, celluloseacetate trimellitate, hydroxypropyl methyl cellulose (HPMC), hydroxypropyl cellulose, hydroxyethyl cellulose, methyl cellulose, specifically HPMCAS or HPMC.

According to another embodiment of the invention, the particulate formulation optionally comprises a component (c) selected from the group consisting of polyalkylene glycol fatty acid esters, polyoxyalkylene glycol fatty alcohol ethers, polyoxyalkylene glycols, poloxamers, and polyoxyalkylene glycol glycerides. Another class of suitable components (c) are alkylene glycol fatty acid mono or diesters. Specific examples are polyoxyl 15 hydroxystearat, polyoxyl 40 hydrgogenated castor oil, polyethylene glycol with a molecular weight in the range from 300 to10,000, polyoxyethylene stearylether, polyoxyethylene laurylether, and polyoxyethylene cetylether.

According to another embodiment, the particulate composition optionally comprises a component (d) selected from the group consisting of antioxidants, chelating agents, colorants, flavours, fillers, stabilizers, preservatives/biocides. Suitable examples are natural or synthetic tocopherols, ascorbic acid, ethylenediamintetraacetic acid tetrasodium salt, silica, talc, magnesium stearate, or butylated hydroxytoluene. In one or more embodiments, the biocide comprises silver ions. Other suitable preservatives are parahydroxy benzoic acid esters, benzoic acid salts, sorbic acid, benzalkonium chloride, Thiomersal, citric acid and its salts, propionic acid and its salts. Also ethanol or propylene glycol can be used as preservatives in concentrations of more than 15% b.w. of the solution.

In one or more embodiments, the particulate formulations according to the invention consist of
 (a) 5 to 20% b.w. of at least one water-soluble Vitamin E-derivative,
 (b) 80 to 95% b.w. of at least one hydrophilic polymer,
 (c) 0 to 15% b.w. of additional surface-active substances, and
 (d) 0 to 15% b.w. of additional pharmaceutical additives, with the proviso that the total amount of (a), (b) and optionally (c) and/or (d) equals 100% b.w. of the formulation, and wherein the fines fraction of the particulates is less than 10% b.w. of particulates with a diameter below 100 μm.

In specific embodiments, the particulate formulations consist of
 (a) 10 to 20% b.w. of at least one water-soluble Vitamin E-derivative,
 (b) 80 to 90% b.w. of at least one hydrophilic polymer,
 (c) 0 to 15% b.w. of additional surface-active substances, and
 (d) 0 to 15% b.w. of additional pharmaceutical additives. With the proviso, that the sum of (a), (b), (c) and (d) equals 100% by weight of the formulation, and wherein the fines fraction of the particulates is less than 10% b.w. of particulates with a diameter below 100 μm.

According to an embodiment, the particulate formulation consists of:
 (a) 10 to 20% b.w. of at least one tocopheryl polyethylene glycol succinate (TPGS)
 (b) 80 to 90% b.w. of at least one hydrophilic polymer,
 (c) 0 to 15% b.w. of additional surface-active substances, and
 (d) 0 to 15% b.w. of additional pharmaceutical additives, with the proviso, that the sum of (a), (b), (c) and (d) equals 100% by weight of the formulation, and wherein the fines fraction of the particulates is less than 10% b.w. of particulates with a diameter below 100 μm. In specific embodiments, component (a) comprises TPGS 1000.

According to another embodiment, the particulate formulations consist of:
 (a) 10 to 20% b.w. of at least one TPGS,
 (b) 80 to 90% b.w. of a polyacrylate,
 (c) 0 to 15% b.w. of additional surface-active substances, and
 (d) 0 to 15% b.w. of additional pharmaceutical additives, with the proviso, that the sum of (a), (b), (c) and (d) equals 100% by weight of the formulation, and wherein the fines fraction of the particulates is less than 10% b.w. of particulates with a diameter below 100 μm. In specific embodiments, the TPGS is TPGS 1000. In a specific embodiment, component (b) is a copolymer of ethyl acrylate and methacrylic acid in a ratio of 1:1, or copolymers of methyl methacrylate and methacrylic acid in ratios of 1:1 and 2:1 or terpolymers of ethyl acrylate, methyl methacrylate and trimethylammonioethyl methacrylate in ratios of 1:2:0.2 or 1:2:0.1.

According to another embodiment, the particulate formulations consist of:
 (a) 10 to 20% b.w. of at least one TPGS,
 (b) 80 to 90% b.w. of a cellulose derivative, (c) 0 to 15% b.w. of additional surface-active substances, and (d) 0 to 15% b.w. of additional pharmaceutical additives, with the proviso, that the sum of (a), (b), (c) and (d) equals 100% by weight of the formulation, and wherein the fines fraction of the particulates is less than 10% b.w. of particulates with a diameter below 100 µm. In a specific embodiment, the TPGS is TPGS 1000.

According to another embodiment, the particulate formulations consist of:

(a) 10 to 20% b.w. of at least one TPGS, (b) 80 to 90% b.w. of a copolymer of N-vinyl caprolactam, vinyl acetate and polyethylenglycol, (c) 0 to 15% b.w. of additional surface-active substances, and (d) 0 to 15% b.w. of additional pharmaceutical additives, with the proviso, that the sum of (a), (b), (c) and (d) equals 100% by weight of the formulation, and wherein the fines fraction of the particulates is less than 10% b.w.-% of particulates with a diameter below 100 µm. In a specific embodiment, the TPGS is TPGS 1000. In a specific embodiments, component (b) is a copolymer of N-vinyl caprolactam, vinyl acetate and polyethylene glycol 6000 with K-values in the range of from 25 to 50, preferably in a weight ratio of 57:30:13 with a K-value of 31 to 41 (1% b.w. solution in ethanol).

According to one or more embodiments, the particulate formulations consist of (a) 10 to 20% b.w. of at least one TPGS, (b) 80 to 90% b.w. of a copolymer of N-vinyl pyrrolidone and vinyl acetate, (c) 0 to 15% b.w. of additional surface-active substances, and (d) 0 to 15% b.w. of additional pharmaceutical additives, with the proviso, that the sum of (a), (b), (c) and (d) equals 100% by weight of the formulation, and wherein the fines fraction of the particulates is less than 10% b.w. of particulates with a diameter below 100 µm. In a specific embodiment, the TPGS is TPGS 1000.

A specific embodiment relates to a particulate formulation consisting of (a) 10 to 15% b.w. of at least one TPGS, (b) 85 to 90% b.w. of a copolymer of N-Vinyl pyrrolidone and vinyl acetate, (c) 0 to 15% b.w. of additional surface-active substances, and (d) 0 to 15% b.w. of additional pharmaceutical additives, with the proviso, that the sum of (a), (b), (c) and (d) equals 100% by weight of the formulation, and wherein the fines fraction of the particulates is less than 10% b.w. of particulates with a diameter below 100 µm. According to this embodiment, component (b) is obtained from 6 parts of N-vinyl pyrrolidone and 4 parts of vinyl acetate. In specific embodiments, the TPGS is TPGS 1000.

Independently of which of the above described embodiments is chosen for the inventive particulate formulations, the formulations do not comprise a pharmaceutically active ingredient. The vitamin E derivative used according to the invention is used as a surfactant, but it can also serve as an active ingredient. Insofar the statement that the particulate formulations "do not comprise pharmaceutically active ingredient" means no pharmaceutically active ingredient other than the water-soluble vitamin E derivative.

The inventive particulate formulation is not a physical mixture of the components, but a formulated composition wherein the components cannot be separated from each other by mechanical processes, such as for instance sieving.

According to one or more embodiments, the inventive particulate formulations are obtained by a spray drying agglomeration process, characterized by the following steps:

(i) forming an aqueous solution of components (a), (b) and optionally (c) and (d), (ii) atomizing said solution with the help of one or more spray nozzles, contacting the atomized solution with particulate material consisting of components (a), (b) and optionally (c) and (d), and recovery of the dried particulate material.

According to an embodiment, the spray drying agglomeration process for manufacturing a particulate formulation according to the invention is characterized by the following steps:

(i) forming an aqueous solution of components (a), (b) and optionally (c) and (d), (ii) atomizing said solution with the help of an atomizing device in a spray tower, contacting the atomized solution with fines of a particulate material consisting of components (a), (b) and optionally (c) and (d) and (iii) separation of the fines and recirculation of the fines into the tower.

According to another embodiment, the spray drying agglomeration process for manufacturing a particulate formulation according to the invention is characterized by the following steps:

(i) forming an aqueous solution of components (a), (b) and optionally (c) and (d), (ii) atomizing said solution with the help of an atomizing device in a spray tower, contacting the atomized solution with fines of a particulate material consisting of components (a), (b) and optionally (c) and (d) and (iii) separation of fines and recirculation of the fines into the spray tower, and (iv) drying of the particulate formulation in a fluidized bed.

Step (i): Formation of the Spray Solution

Method (i) a): According to one or more embodiments of the invention, step (i), i.e. the formation of the aqueous spray solution, is carried out in such a way that first of all component (a) is dissolved in water at elevated temperatures followed by blending in the solid hydrophilic polymer into the first solution. Optionally components (c) and (d) are also blended into the first solution. As used herein, the phrase "elevated temperatures" means 30 to 60° C., specifically 37 to 55° C. In one or more embodiments, the dissolution of the components is carried out under stirring.

Method (i) b): According to another embodiment, the aqueous spray solution is prepared by dissolving the hydrophilic polymer at ambient temperatures in water and blending in component (a) in solid form. The blending in is preferably carried out under stirring. Optionally the blending in of component (a) can be carried out at elevated temperatures of from 30 to 60° C., specifically from 37 to 55° C.

Method (i) c): According to another embodiment, component (a) is molten and blended into an aqueous solution of the hydrophilic polymer. The melting of component (a) can be carried out at 40 to 75° C., specifically at 55 to 65° C. In one or more embodiments, blending in the melt is carried out under stirring.

Method (i) d): According to yet another embodiment, a first solution of component (a) is formed at ambient temperatures or, specifically, at the above mentioned (Method (i) a) or b)) elevated temperatures. A second separate aqueous solution of the hydrophilic polymer is formed. The second solution can be formed at ambient temperatures. The resulting spray solution can be formed in a batch process either by blending in the first solution of component (a) into the second solution or by blending in the second solution into the first solution.

Method (i) e): In one or more embodiments, the first and the second solution can also be blended in a continuous process, for instance by mixing a stream of the first solution with a stream of the second solution in a continuous mixing chamber.

In specific embodiments, an aqueous solution of the hydrophilic polymer (b) is blended into an aqueous solution of component (a) as described in connection with Method (i) d).

Independently of which of the Methods (i) a), b), c), d) or e) is used, the following conditions apply and can be combined where applicable:

The solids content of the spray solution can vary from 10 to 50% b.w., specifically from 20 to 40% b.w., more specifically from 20 to 35% b.w.

The concentration of the vitamin E derivative in the aqueous solution can range from 5 to 22% b.w., specifically from 8 to 19% b.w., and more specifically from 9-17% b.w.

The spray solution can be stored for several hours or overnight before being introduced into the spray drying agglomeration apparatus. The temperature of the stored solutions can be maintained in the range of from 37° C. to 60° C., specifically from 40° C. to 55° C. and more specifically from 48 to 52° C. In specific embodiments, the spray solution is kept stirring during the storage period.

Additional components such as the optional components (c) or (d) can be blended into the readymade spray solution comprising components (a) and (b) as such or in the form of an aqueous solution or dispersion.

Step (ii): Spray Drying Agglomeration

According to one or more embodiments, the inventive particulate formulation is obtained by a process known as spray drying-agglomeration. A spray drying-agglomeration process is characterized by a type of agglomeration known as a forced secondary agglomeration. A spray solution is atomized and agglomeration is controlled by returning fines to the atomized cloud. By definition, fines are the cyclone or bag filter fractions or fractions separated by a particular air flow where they do not sediment anymore and consist of the smallest particulates which are recycled to the process. In one or more embodiments, according to Method (ii) a) the recycled dry fines are introduced into the spray tower near the atomizing nozzle(s) in the upper part of the spray apparatus where they will collide with the atomized droplets of the spray solution and thus form agglomerates. In one or more embodiments, the particle diameter of such fines is below 100 μm. As used herein, the phrase "upper part of the spray apparatus" means the upper 20 Vol.-% of the spray tower or spray apparatus. By introducing the fines near the atomizing devices such as nozzle(s) or a rotating disc, the contact between fines and atomized droplets is particularly enhanced.

In one or more embodiments, method (ii) a) is combined with Step (iii), i.e. the recirculation of separated fines.

In one or more embodiments, according to Method (iv), a fluidized bed can be operated at the bottom of the spray apparatus. The resulting particulate formulation can be subjected to further drying in such a fluidized bed.

According to a specific embodiment, Methods (ii) a) and (iii) and (iv) are combined, particularly in combination with Method (i) d).

In one or more embodiments, the invention relates to a spray drying agglomeration process for a particulate formulation consisting of (a) 10 to 15% b.w. of at least one TPGS,
(b) 85 to 90% b.w. of a copolymer of N-Vinyl pyrrolidone and vinyl acetate,
(c) 0 to 15% b.w. of additional surface-active substances, and
(d) 0 to 15% b.w. of additional pharmaceutical additives, with the proviso, that the sum of (a), (b), (c) and (d) equals 100% by weight of the formulation, and wherein the fines fraction of the particulates is less than 10% b.w. of particulates with a diameter below 100 μm, which process is characterized by a combination of Methods (i) d), (ii) a), (iii) and (iv).

According to this process embodiment, component (b) is obtained from 6 parts of N-vinyl pyrrolidone and 4 parts of vinyl acetate. In specific embodiments, the TPGS is TPGS 1000.

The resulting particulates have a distinctive raspberry-like shape, sometimes also called blackberry-like shape.

Independently of which embodiment is used, the following conditions for spray drying agglomeration apply:

The drying gas can be air, nitrogen or any other inert gas. In one or more embodiments, air is used as drying gas. The drying gas is usually introduced at the top of the apparatus. According to one embodiment, the major part of the drying gas is introduced at the top of the apparatus, and the minor part of the drying gas is introduced into a fluidized bed located at the bottom of the apparatus. A major part of the drying gas can be 60 to 90% b.w. of the gas. The amount of gas flow depends on the dimensions of the apparatus. The temperature of the drying gas usually lies in the range of 60 to 200° C., specifically from 85 to 130° C., for the inlet temperature at the top of the spray drying apparatus. The temperature of the drying gas which is introduced into the fluidized bed located at the bottom of the spray apparatus usually lies in the range of 20 to 80° C., specifically from 45 to 60° C. for the inlet temperature. The outlet temperature lies in the range of from 35 to 90° C., specifically from 45 to 70° C.

In one or more embodiments, spraying is performed with single component or two component nozzles. Alternatively, rotating discs can be used. Single component nozzles operate typically in the range of 2-20 MPa atomizing pressure whereas two component nozzles use compressed air at 0.05-1 MPa.

According to a specific embodiment, the inventive process is carried out in such a way that a fluidized bed is operated at the bottom of the spray apparatus. In one or more embodiments, the temperature within the fluidized bed is kept below the melting temperature of component (a).

The amount of returned fines compared to spray velocity and gas flow depends on the dimensions of the apparatus.

The dried agglomerates are classified and the fines are returned into the apparatus.

The resulting inventive particulate formulation is stable in the packing on storage even at elevated temperatures such as 40° C. for at least three months.

Formulations according to any of the inventive embodiment can be tested for stability by measuring the firmness of the stored material in a water-tight packaging with a penetrometer. The penetrometer test measures the force necessary for pressing a cone under defined conditions into the store packaged material. This method can be used to control storage stability of a given packaged material.

According to one or more embodiments, after four weeks of storage at 40° C. and 10% relative humidity, the firmness is less than 1 N measured by 6 mm cone penetrometer. The firmness measured by using a 12 mm cone penetrometer is less than 3 N.

The inventive particulate formulation can be used to give pharmaceutical formulations or dosage forms by processing the particulate formulation together with one or more pharmaceutically active ingredients and optionally other excipients or additives.

One method for processing the inventive particulate formulation together with other ingredients to give a pharmaceutical formulation or dosage form is the melt-extrusion process. The melt-extrusion process comprises the steps of preparing a homogeneous melt of the active ingredient or the combination of active ingredients, the pharmaceutically acceptable polymer and the inventive particulate formulation, and cooling the melt until it solidifies. As used herein, the term "melting" means a transition into a liquid or rubbery state in which it is possible for one component to become homogeneously embedded in the other. Typically, one component will melt and the other components will dissolve in the melt, thus forming a solution. Melting usually involves heating above the softening point of the pharmaceutically acceptable polymer. The preparation of the melt can take place in a variety of ways. The mixing of the components can take place before, during or after the formation of the melt. For example, the components can be mixed first and then melted or simultaneously mixed and melted. Usually, the melt is homogenized in order to disperse the active ingredients efficiently. Also, it may be convenient first to melt the inventive particulate formulation and then to admix and homogenize the active ingredients.

In one or more embodiments, usually, the melt temperature (mass temperature) lies in the range of 100 to 350° C., specifically 100 to 300° C. If one or more lubricants is added, the lower temperature can be 50° C.

According to one or more embodiments, the active ingredients can be employed as such or as a solution or dispersion in a suitable solvent such as alcohols, aliphatic hydrocarbons or esters. Another solvent which can be used is liquid carbon dioxide. The solvent is removed, e.g. evaporated, upon preparation of the melt. Various additives may be included in the melt, for example flow regulators such as colloidal silica; lubricants, bulking agents (fillers), plasticizers, stabilizers such as antioxidants, light stabilizers, radical scavengers, or stabilizers against microbial attack. The melting and/or mixing takes place in an apparatus customary for this purpose. Particularly suitable are extruders or kneaders. Suitable extruders include single screw extruders, intermeshing screw extruders or else multi-screw extruders, preferably twin screw extruders, which can be co-rotating or counter-rotating and, optionally, equipped with kneading disks or other screw elements for mixing or dispersing the melt. The working temperatures will also be determined by the kind of extruder or the kind of configuration within the extruder used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components. The melt is extruded through a die system.

According to one or more embodiments, the extrudate leaving the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. Another option is to form films by calendering. Alternatively, the extrudate is moulded into the desired shape by injection-moulding. Alternatively, the extrudate is subjected to profile extrusion and cut into pieces, either before (hot-cut) or after solidification (cold-cut). Additionally, foams can be formed if the extrudate contains a propellant such as a gas, e.g. carbon dioxide, or a volatile compound, e.g. a low molecular-weight hydrocarbon, or a compound that is thermally decomposable to a gas. The propellant is dissolved in the extrudate under the relatively high pressure conditions within the extruder and, when the extrudate emerges from the extruder die, the pressure is suddenly released. Optionally, the resulting solid solution product is milled or ground to granules. The granules may then be filled into capsules or may be compacted. As used herein, the term "compacting" refers to a process whereby a powder mass comprising the granules is densified under high pressure in order to obtain a compact with low porosity, e.g. a tablet. Compression of the powder mass is usually done in a tablet press, more specifically in a steel die between two moving punches.

Alternatively the particulate formulation according to the invention can be formulated with other pharmaceutical ingredients by a melt-granulation process. In a melt granulation process, the material is not converted to a homogeneous melt. The material is only heated to the extent that the surface of the inventive particulate formulation is molten so that the particulates get tacky and start to adhere together. The melt granulation process can be carried out in a high-shear mixer or in an extruder which is operated without a die system. Since the extruder is in this case operated with an open discharge no pressure is build up within the extruder.

In one or more embodiments, at least one additive selected from flow regulators, bulking agents (fillers) and lubricants is used in compacting the granules.

According to one or more embodiments, suitable bulking agents (also referred to as "fillers") are selected from lactose, calcium hydrogenphosphate, microcrystalline cellulose (Avicel®), magnesium oxide, potato or corn starch, isomalt, polyvinyl alcohol. Suitable flow regulators are selected from highly dispersed silica (Aerosil®), and animal or vegetable fats or waxes.

In one or more embodiments, a lubricant is used in compacting the granules. Suitable lubricants are selected from polyethylene glycol (e.g., having a Mw of from 1000 to 6000), magnesium and calcium stearates, sodium stearyl fumarate, talc and the like.

The inventive particulate formulations are particularly suitable for preparing pharmaceutical dosage forms comprising active ingredients with a solubility in water of less than 0.1%, specifically of less than 0.01% (g/g) at 20° C. and normal pressure.

According to one or more embodiments, the active ingredients may come from any range of indications.

Non-limiting examples which may be mentioned here are benzodiazepines, antihypertensives, vitamins, cytostatics—especially Taxol, anesthetics, neuroleptics, antidepressants, agents having antiviral activity, such as, for example, agents having anti-HIV activity, antibiotics, antimycotics, antidementia agents, fungicides, chemotherapeutics, urologicals, platelet aggregation inhibitors, sulfonamides, spasmolytics, hormones, immunoglobulins, sera, thyroid therapeutics, psychoactive drugs, antiparkinson agents and other antihyperkinetics, ophthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynecologicals, gout remedies, fibrinolytics, enzyme products and transport proteins, enzyme inhibitors, emetics, blood flow stimulators, diuretics, diagnostic aids, corticoids, cholinergics, biliary therapeutics, anti asthmatics, bronchodilators, beta-receptor blockers, calcium antagonists, ACE inhibitors, arteriosclerosis remedies, antiinflammatory drugs, anticoagulants, antihypertensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

In one or more embodiments, the inventive particulate formulations can be used in a melt-extrusion process without showing any of the known disadvantages of prior art formulations. The particulate formulations are easily mixable with other compounds in particular with actives leading to so-called interactive mixtures which do not show segregation. Thus, a second feeder for the active is not necessary making the extrusion process easier. Surprisingly, the throughput rate of the extruder can be adjusted to extremely high values. Thus, on a 16 mm extruder at 200 rpm and a temperature of 150° C., more than 5.5 kg/h can be run, by far higher than the rates of the single components (Single components can be extruded on a 16 mm extruder at 200 rpm and a temperature of 160° C. only with less than 4 kg/h).

Surprisingly, the inventive formulations do not lead to any dust formation. In addition, they are characterized by an excellent flowability, which is maintained even when storing the material at elevated temperatures (40° C.) for a long period of time (8 weeks). Usually, such soft materials and, in particular, materials with a small particle size of more than 10% b.w. below 100 µm show stickiness and cold flow behavior preventing it from a good flowability.

The inventive formulation and so called interactive mixtures thereof can be used in a direct compression process to manufacture tablets. Surprisingly, there is no sticking of the powder to the tablet punch which normally is likely to happen when physical mixtures with low melting substances are compressed.

The inventive formulation and so-called interactive mixtures of thereof can be used for roller compaction. Surprisingly it is possible to process the formulation in the compactor, even though a low melting substance is contained. Physical mixtures of the components cannot be processed because the low melting substance will stick to the rolls.

The inventive formulation and so-called interactive mixtures can be used in wet granulation processes (high shear granulation and fluid bed granulation). Surprisingly, the content uniformity of the granulated product can be achieved easily According to one or more embodiments, the following methods can be used to characterize the physical properties of the particulate formulations.

Particle Size:

The analysis is performed with a Malvern Mastersizer 2000 Vers 5.22, Malvern Instruments, UK). The product is put on the sample plate (vibration intensity 100%) and dispersed with air a pressure of 0.05 MPa. The measurement is carried out with an obscuration between 3-10%

Bulk Density:

The bulk density is the ratio of mass of an untapped powder sample to its volume. The powder is poured into a measuring cylinder of 150 ml and excess powder is discarded with a spatula. The mass of 150 ml Powder is obtained by differential weighing.

Angle of Repose:

The angle of repose is a characteristic related to resistance to movement between particles. It is the constant, three dimensional angle (relative to the horizontal base) assumed by a cone-like pile of material that is formed by draining excess quantity through a funnel by the method described below.

150 ml of untapped powder is filled into a measuring cylinder of 150 ml and excess powder is discarded with a spatula. The powder is poured into a funnel (Pfrengle type, diameter 1 cm), of which the opening is closed. The powder is drained from the funnel (if necessary under stirring with 1 rps) to a plate (diameter 10 cm, height 2.5 cm). The angle of repose is calculated from the relation of the height of the powder pile and the radius of the plate.

Sieve Analysis

The degree of fineness of a powder can be expressed by reference to a sieve. The sieve analysis is performed with an Retsch AS 200 control sieving machine (100 g powder; amplitude: 1.0; sieving time: 10 min, without sieving aids or interruption). Separated fractions are determined by differential weighing.

The invention is now described with reference to the following examples.

EXAMPLES

Example 1

Formulation Comprising 15% b.w. TPGS 1000

62 kg water were heated to a temperature of 50° C. 9 kg molten TPGS (Temperature 60° C.) are added under gentle stirring at low intensity (paddle, 250 rpm) and continuous heating (50° C.) with a paddle stirrer. The stirrer was covered by the solution to avoid foaming. After 60 minutes of stirring TPGS was completely dissolved. 138 kg Copovidon solution with a solid content of 37% b.w. were added under gentle stirring. The mixture was stirred for 15 minutes. The resulting solution was clear and transferred under continuous stirring to the dryer. The solids content was adjusted to 20% b.w. by adding water.

Spray Drying Agglomeration Conditions:

| | |
|---|---|
| Apparatus: | SBD dryer, Anhydro, height 2 m, diameter 1.2 m, two component nozzle; equipped with device for introducing fines and with a fluidized bed at the bottom |
| Solid content of the spray solution: | 20% b.w. |
| Temperature of the gas, inlet tower: | 93° C. |
| Temperature of the gas, fluidized bed: | 45° C. |
| Amount of drying gas, inlet tower: | 450 kg/h |
| Amount of drying gas, fluidized bed: | 120 kg/h |
| Temperature exhaust air: | 50° C. |
| Nozzle gas, pressure: | 0.15 MPa |
| Flow rate of solution: | 11.4 kg/h |

The particulate material was characterized as follows:

Angle of repose: 43°; bulk density: 0.33 g/cm$^3$,

Not more than 10% by weight of the sample passed the 100 µm sieve.

Particle sizes: d(0.1): 136 µm; d(0.5):250 µm; d(0.9):426 µm; D[4,3]: 266 µm

Example 2

Formulation Comprising 10% b.w. TPGS 1000

54 kg water were heated to a temperature of 50° C. 6 kg molten TPGS (Temperature 60° C.) were added under gentle stirring (paddle, 250 rpm) and continuous heating (50° C.) with a paddle stirrer. The stirrer was covered by the solution to avoid foaming. After 60 minutes of stirring TPGS was completely dissolved. 146 kg Copovidon Solution with a solid content of 37% are added under gentle stirring. The mixture was stirred for 15 minutes. The resulting solution was clear and transferred under continuous stirring to the spray apparatus.

Spray Drying Agglomeration Conditions:

| Apparatus: | SBD dryer, Anhydro, height 2 m, diameter 1.2 m, two component nozzle; equipped with device for introducing fines and with a fluidized bed at the bottom |
|---|---|
| Solid content of the solution: | 30% b.w. |
| temperature of the gas, inlet tower: | 93° C. |
| temperature of the gas, fluidized bed: | 45° C. |
| Amount of drying gas, inlet tower: | 450 kg/h |
| Amount of drying gas, fluidized bed: | 120 kg/h |
| Temperature exhaust air: | 50° C. |
| Nozzle gas, pressure: | 0.15 MPa |
| Flow rate of solution: | 11.4 kg/h |

The particulate material was characterized as follows:
Angle of repose: 44°; bulk density: 0.31 g/cm$^3$;
Particle sizes: d(0.1): 133 μm; d(0.5): 246 μm; d(0.9): 420 μm D[4,3]: 262 μm Not more than 10 weight % of the sample passed the 100 μm sieve.

Comparative Example A

Preparation of a Spray Dried Product

A spray solution according to Example 1 was introduced into a spray drying apparatus with two component nozzles. The solution was sprayed under the following conditions:

| Apparatus | Nubilosa spray tower, height 12 m, diameter 0.8 m |
|---|---|
| Solid content of the solution | 25% b.w. |
| Temperature of the gas, inlet | 115° C. |
| Temperature exhaust air | 55° C. |
| Amount of drying gas | 450 kg/h |
| Pressure of nozzle gas | 1.8 bar |
| Flow rate of solution | 6.5 kg/h |

Particle sizes: d(0.1): 30 μm; d(0.5): 83 μm; d(0.9): 168 μm D[4,3]: 93 μm

An angle of repose could not be measured due to the poor flowability of the product.

The firmness of the products according to examples 1 to 2 and Comparative Example A was determined with a cone penetrometer as described below.

Test Method Penetrometer

The particulate material according to the invention was packed into aluminium foil laminated polyethylene inliner bags (100 μm) of size DIN A 5. The bags were stored in a climate chamber with a relative humidity of 10% either at 30° C. or 40° C. for 10 days, 4 weeks, 8 weeks. The bags were stored with a compression load of 2.2 kPa. After the pre-determined storage time the bags were opened in such a way that the compressed material remained undisturbed.

The firmness of the material was tested with a 6 mm or 12 mm cone tipped penetrometer by determining the force (in [N]) needed to insert the cone for 6 mm or 12 mm into the material.

The penetrometer used according to the examples was a digital mobile force meter PCE-FM 200, PCE Deutschland GmbH.

The results are depicted in the table below.

TABLE I

Storage Stability, Cone Penetrometer Test, Firmness in [N]

| | 10% TPGS | 15% TPGS | Comp. Ex. A |
|---|---|---|---|
| 10 days, 30° C., 6 mm cone | 0.07 | 0.15 | — |
| 10 day, 30° C., 12 mm cone | 0.39 | 0.95 | — |
| 4 weeks, 30° C., 6 mm cone [N] | 0.13 | 0.68 | — |
| 4 weeks, 40° C., 6 mm cone [N] | 0.72 | 0.97 | 2.0 |
| 4 weeks, 30° C., 12 mm cone [N] | 0.68 | 2.06 | — |
| 4 weeks, 40° C., 12 mm cone [N] | 2.06 | 2.96 | 8.1 |
| 8 weeks, 30° C., 6 mm cone | 0.23 | 0.73 | — |
| 8 weeks, 40° C., 6 mm cone | 1.61 | 0.71 | 1.5 |
| 8 weeks, 30° C., 12 mm cone | 0.86 | 1.35 | — |
| 8 weeks, 30° C., 12 mm cone | 2.56 | 1.96 | 8.0 |

Example 3

Comparison of Material Throughput in a Melt Extrusion Process

The product according to Example 1 was melt-extruded with a 16 mm Thermofisher Polylab Extruder. For comparison, the single components, i.e. Kollidon VA 64 and TPGS 1000 were melt-extruded as well.

The product according to Ex. 1 could be extruded at 200 rpm and a temperature of 150° C. with a throughput of more than 5.5 kg/h. The single components could be extruded at 200 rpm and a temperature of 160° C. only with a throughput less than 4 kg/h.

Example 4

Formulation Comprising 5% b.w. TPGS 1000

45 kg water were heated to a temperature of 50° C. 3 kg molten TPGS (Temperature 60° C.) were added under gentle stirring at low intensity (paddle, 250 rpm) and continuous heating (50° C.) with a paddle stirrer. The stirrer was covered by the solution to avoid foaming. After 60 minutes of stirring TPGS was completely dissolved. 154 kg Copovidon solution with a solid content of 37% b.w. were added under gentle stirring. The mixture was stirred for 15 minutes.

The solids content was adjusted to 28% b.w. by adding water. The resulting solution was clear and transferred under continuous stirring to the dryer Spray Drying Agglomeration Conditions:

| Apparatus: | SBD dryer, Anhydro, height 2 m, diameter 1.2 m, two component nozzle; equipped with device for introducing fines and with a fluidized bed at the bottom |
|---|---|
| Solid content of the spray solution: | 28% b.w. |
| Temperature of the gas, inlet tower: | 93° C. |
| Temperature of the gas, fluidized bed: | 45° C. |

| Amount of drying gas, inlet tower: | 450 kg/h |
|---|---|
| Amount of drying gas, fluidized bed: | 120 kg/h |
| Temperature exhaust air: | 50° C. |
| Nozzle gas, pressure: | 0.15 MPa |
| Flow rate of solution: | 11.4 kg/h |

The particulate material was characterized as follows:
Angle of repose: 44°; bulk density: 0.30 g/cm$^3$,
Not more than 10% by weight of the sample passed the 100 μm sieve.
Particle sizes: d(0.1): 110 μm; d(0.5):237 μm; d(0.9):405 μm; D[4,3]: 216 μm

Example 5

Formulation Comprising 20% b.w. TPGS 1000

70 kg water was heated to a temperature of 50° C. 12 kg molten TPGS (Temperature 60° C.) were added under gentle stirring at low intensity (paddle, 250 rpm) and continuous heating (50° C.) with a paddle stirrer. The stirrer was covered by the solution to avoid foaming. After 60 minutes of stirring TPGS was completely dissolved. 130 kg Copovidon solution with a solid content of 37% b.w. were added under gentle stirring. The mixture was stirred for 15 minutes. The solids content was adjusted to 25% b.w. by adding water. The resulting solution was clear and transferred under continuous stirring to the dryer Spray Drying Agglomeration Conditions:

| Apparatus: | SBD dryer, Anhydro, height 2 m, diameter 1.2 m, two component nozzle; equipped with device for introducing fines and with a fluidized bed at the bottom |
|---|---|
| Solid content of the spray solution: | 25% b.w. |
| Temperature of the gas, inlet tower: | 90° C. |
| Temperature of the gas, fluidized bed: | 43° C. |
| Amount of drying gas, inlet tower: | 450 kg/h |
| Amount of drying gas, fluidized bed: | 120 kg/h |
| Temperature exhaust air: | 50° C. |
| Nozzle gas, pressure: | 0.15 MPa |
| Flow rate of solution: | 11.4 kg/h |

The particulate material was characterized as follows:
Angle of repose: 45°; bulk density: 0.35 g/cm$^3$,
Not more than 10% by weight of the sample passed the 100 μm sieve.
Particle sizes: d(0.1): 123 μm; d(0.5):260 μm; d(0.9):425 μm; D[4,3]: 248 μm
The particulate material was tested for storage stability according to the cone penetrometer test as described above. The results are depicted in the table below. The product with 5% b.w. of TPGS was not tested, because the firmness of the material is influenced by the TPGS content in the formulation. A product with only 5% b.w. TPGS is at least as stable as a product with 10% b.w. TPGS.

TABLE II

Storage Stability, Cone Penetrometer Test, Firmness in [N]

| | Product with 20% TPGS |
|---|---|
| 10 days, 30° C., 6 mm cone | 0.25 |
| 10 day, 30° C., | 1.5 |

TABLE II-continued

Storage Stability, Cone Penetrometer Test, Firmness in [N]

| | Product with 20% TPGS |
|---|---|
| 12 mm cone | |
| 4 weeks, 30° C., 6 mm cone [N] | 0.9 |
| 4 weeks, 40° C., 6 mm cone [N] | 1.8 |
| 4 weeks, 30° C., 12 mm cone [N] | 2.33 |
| | 5 |
| 4 weeks, 40° C., 12 mm cone [N] | 3.5 |
| 8 weeks, 30° C., 6 mm cone | 2.57 |
| 8 weeks, 40° C., 6 mm cone | 3.8 |
| | 10 |
| 8 weeks, 30° C., 12 mm cone | 3.1 |
| 8 weeks, 40° C., 12 mm cone | 4.5 |

All references, including publications, patent applications, and patents, cited herein are hereby incorporated by reference for all purposes to the same extent as if each reference were individually and specifically indicated to be incorporated by reference and were set forth in its entirety herein.

The use of the terms "a" and "an" and "the" and similar referents in the context of describing the materials and methods discussed herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the materials and methods and does not pose a limitation on the scope unless otherwise claimed. No language in the specification should be construed as indicating any non-claimed element as essential to the practice of the disclosed materials and methods.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims.

What is claimed is:

1. A storage-stable dust-free homogeneous spray-dried agglomerated formulation, consisting of:
   (a) at least one water-soluble Vitamin E-derivative; and
   (b) at least one hydrophilic polymer;
   with the proviso, that the sum of (a) and (b) equals 100% by weight of the formulation,
   wherein a fines fraction of the agglomerated formulation is less than 10% by weight with a particle diameter of less than 100 μm,
   wherein the agglomerated formulation is free of organic solvents, and
   wherein the agglomerated formulation is an agglomerate produced by a spray drying agglomeration process.

2. The formulation of claim 1, wherein the average particle size $D_{0[4,3]}$ is from 100 μm to 800 μm.

3. The formulation of claim 1, wherein the component (a) is a tocopheryl polyethylenglycol succinate.

4. The formulation of claim 1, wherein the component (b) is selected from the group consisting of homo- or copolymers of a N-vinyl lactam, cellulose derivatives, polyacrylic polymers, polyalkylene oxides, polyvinyl alcohols, and oligo- and polysaccharides.

5. The formulation of claim 4, wherein the component (b) comprises a homo- or copolymer of a N-vinyl lactam.

6. The formulation of claim 1, wherein the component (b) comprises a homo- or copolymer of N-vinyl pyrrolidone.

7. The formulation of claim 1, wherein the component (b) comprises a copolymer of N-vinyl pyrrolidone and vinyl acetate.

8. The formulation of claim 1, wherein the component (b) comprises a copolymer of N-vinyl caprolactam, vinyl acetate and polyethylene glycol.

9. The formulation of claim 4, wherein the component (b) comprises a cellulose derivative.

10. A storage-stable dust-free homogeneous spray-dried agglomerated formulation, consisting of:
    (a) at least one water-soluble Vitamin E-derivative;
    (b) at least one hydrophilic polymer; and
    (c) at least one surface-active substance selected from the group consisting of polyalkylene glycol fatty acid esters, polyalkylene glycol fatty alcohol ethers, polyalkylene glycols, poloxamers, polyalkylene glycol glycerides, and alkylene glycol fatty acid mono- and diesters;
    with the proviso, that the sum of (a), (b), and (c) equals 100% by weight of the formulation,
    wherein the at least one surface-active substance is present in the formulation in an amount up to 15% by weight of the formulation,
    wherein a fines fraction of the agglomerated formulation is less than 10% by weight with a particle diameter of less than 100 μm,
    wherein the agglomerated formulation is free of organic solvents, and
    wherein the agglomerated formulation is an agglomerate produced by a spray drying agglomeration process.

11. A storage-stable dust-free homogeneous spray-dried agglomerated formulation, consisting of:
    (a) at least one water-soluble Vitamin E-derivative;
    (b) at least one hydrophilic polymer;
    (c) at least one surface-active substance selected from the group consisting of polyalkylene glycol fatty acid esters, polyalkylene glycol fatty alcohol ethers, polyalkylene glycols, poloxamers, polyalkylene glycol glycerides, and alkylene glycol fatty acid mono- and diesters; and
    (d) at least one pharmaceutical additive selected from the group consisting of antioxidants, chelating agents, colorants, flavors, fillers, stabilizers, preservatives, and biocides;
    with the proviso, that the sum of (a), (b), (c), and (d) equals 100% by weight of the formulation,
    wherein the at least one surface-active substance is present in the formulation in an amount up to 15% by weight of the formulation,
    wherein the at least one pharmaceutical additive is present in the formulation in an amount up to 15% by weight of the formulation,
    wherein a fines fraction of the agglomerated formulation is less than 10% by weight with a particle diameter of less than 100 μm,
    wherein the agglomerated formulation is free of organic solvents, and
    wherein the agglomerated formulation is an agglomerate produced by a spray drying agglomeration process.

12. The formulation of claim 11, wherein the component (d) is selected from the group consisting of ascorbic acid, tocopherol, and butyl hydroxyl toluene.

13. The formulation of claim 1, wherein:
    the at least one water-soluble Vitamin E-derivative is present in the formulation in an amount of 5 to 20% by weight of the formulation; and
    the at least one hydrophilic polymer is present in the formulation in an amount of 80 to 95% by weight of the formulation.

14. The formulation according to claim 13, wherein:
    the at least one water-soluble Vitamin E-derivative is present in the formulation in an amount of 10 to 20% by weight of the formulation; and
    the at least one hydrophilic polymer is present in the formulation in an amount of 80 to 90% by weight of the formulation.

15. A spray drying agglomeration process for manufacturing the agglomerated formulation of claim 1, comprising:
    (i) forming an aqueous solution, free of organic solvents, of components (a) and (b);
    (ii) atomizing said solution with the help of one or more spray nozzles to produce an atomized solution; and
    (iii) contacting the atomized solution with particulate material consisting of components (a) and (b) to provide the agglomerated formulation.

16. The process of claim 15, wherein the agglomerated formulation is obtained by a spray drying agglomeration, characterized by the following steps:
    (i) forming the aqueous solution, free of organic solvents, of components (a) and (b);
    (ii) atomizing said solution with the help of an atomizing device in a spray tower to produce the atomized solution;
    (iii) contacting the atomized solution with fines of a particulate material consisting of components (a) and (b); and
    (iv) separating the fines and recirculating the fines into the tower.

17. The process of claim 16, further comprising:
    (v) drying the agglomerated formulation in a fluidized bed.

18. The process of claim 15, wherein the aqueous solution has a solids content of from 10 to 50% by weight.

19. The process of claim 15, wherein step (i) is carried out by blending an aqueous solution of the hydrophilic polymer (b) into an aqueous solution of component (a).

20. The formulation of claim 1, wherein the agglomerated formulation is produced by a spray drying agglomeration process comprising:
   (i) forming an aqueous solution, free of organic solvents, of components (a) and (b);
   (ii) atomizing said aqueous solution with the help of an atomizing device in a spray tower to produce an atomized solution;
   (iii) contacting the atomized solution with fines of a particulate material consisting of components (a) and (b); and
   (iv) separating the fines and recirculating the fines into the tower to produce the agglomerated formulation.

21. The process of claim 15, wherein the formulation comprises:
   (a) 5 to 20% by weight of the at least one water-soluble Vitamin E-derivative; and
   (b) 80 to 95% by weight of the at least one hydrophilic polymer.

* * * * *